(12) United States Patent
Barry (10) Patent No.: US 10,143,736 B2
(45) Date of Patent: Dec. 4, 2018

(54) METHODS AND MATERIALS FOR PRODUCING IMMUNE RESPONSES AGAINST POLYPEPTIDES INVOLVED IN ANTIBIOTIC RESISTANCE

(71) Applicant: Mayo Foundation for Medical Education and Research, Rochester, MN (US)

(72) Inventor: Michael A. Barry, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 15/332,831

(22) Filed: Oct. 24, 2016

(65) Prior Publication Data

US 2017/0035873 A1 Feb. 9, 2017

Related U.S. Application Data

(63) Continuation of application No. 14/462,099, filed on Aug. 18, 2014, now abandoned, which is a continuation of application No. 13/001,228, filed as application No. PCT/US2009/048018 on Jun. 19, 2009, now abandoned.

(60) Provisional application No. 61/075,881, filed on Jun. 26, 2008.

(51) Int. Cl.

| *A61K 38/16* | (2006.01) |
|---|---|
| *A61K 39/04* | (2006.01) |
| *A61K 39/085* | (2006.01) |
| *C12N 7/00* | (2006.01) |
| *A61K 39/00* | (2006.01) |

(52) U.S. Cl.
CPC ............ *A61K 39/04* (2013.01); *A61K 38/164* (2013.01); *A61K 39/085* (2013.01); *C12N 7/00* (2013.01); *A61K 2039/5256* (2013.01); *A61K 2039/53* (2013.01); *C12N 2710/10034* (2013.01); *C12N 2710/10043* (2013.01); *C12N 2710/10071* (2013.01); *C12N 2800/22* (2013.01)

(58) Field of Classification Search
None
See application file for complete search history.

(56) References Cited

U.S. PATENT DOCUMENTS

| 5,686,590 | A | 11/1997 | Jacob, Jr. et al. | |
|---|---|---|---|---|
| 6,353,093 | B1 | 3/2002 | Burnham et al. | |
| 8,367,055 | B2 | 2/2013 | Talaat et al. | |
| 8,470,338 | B2 * | 6/2013 | Coler | C07K 14/35 424/234.1 |
| 8,546,093 | B2 | 10/2013 | Song et al. | |
| 9,056,913 | B2 * | 6/2015 | Coler | C07K 14/35 |
| 9,655,958 | B2 * | 5/2017 | Coler | C07K 14/35 |
| 9,725,771 | B2 * | 8/2017 | Ecker | C12Q 1/689 |
| 2007/0037163 | A1 | 2/2007 | Doucette-Stamm et al. | |
| 2011/0014240 | A1 | 1/2011 | Barry et al. | |
| 2011/0105531 | A1 | 5/2011 | Massire et al. | |
| 2011/0189217 | A1 * | 8/2011 | Barry | A61K 38/164 424/190.1 |
| 2013/0022997 | A1 | 1/2013 | Huang et al. | |
| 2013/0202642 | A1 | 8/2013 | Talaat et al. | |
| 2014/0314802 | A1 | 10/2014 | Mettens et al. | |
| 2014/0335536 | A1 | 11/2014 | Kirsebom et al. | |
| 2014/0356395 | A1 * | 12/2014 | Barry | A61K 38/164 424/199.1 |
| 2016/0074480 | A1 * | 3/2016 | Shantha | A61K 31/133 514/2.4 |
| 2016/0194688 | A1 * | 7/2016 | Reddington | C12Q 1/6883 506/9 |
| 2016/0201115 | A1 * | 7/2016 | Colman | C12Q 1/689 514/225.5 |
| 2017/0035873 | A1 * | 2/2017 | Barry | A61K 38/164 |
| 2017/0183725 | A1 * | 6/2017 | Daum | C12Q 1/6869 |
| 2017/0196960 | A1 * | 7/2017 | Voss | A61K 39/04 |
| 2017/0340745 | A1 * | 11/2017 | McArthur | A61K 38/12 |

FOREIGN PATENT DOCUMENTS

WO    WO 2013/090294    6/2013

OTHER PUBLICATIONS

CDC Report, TB Elimination (Multidrug-Resistant Tuberculosis (MDR TB), May 2012.*
Ejo et al, Infection, Genetics and Evolution 33 (2015) 314-319.*
Kato-Miyazawa et al, Clin Microbiol Infect 2015; 21: 248.e1-248.e8 article published online: Oct. 13, 2014.*
UKessays, Multidrug Resistant Tuberculosis, Mar. 23, 20115. 2 pages.*
Palomino et al, Antibiotics, 2014, 3:317-340. published: Jul. 2, 2014.*
Tasbiti et al, International J. Mycobacteriology, 2015, 4:96-97. available online: Dec. 23, 2014.*
Iseman, New England J. Medicine, Sep. 9, 1993, 329/11:784-791.*
Burian et al, Expert Rev. Anti Infect. Ther., 2012, 10/9:1037-1047.*
Allen et al., "Finding alternatives to antibiotics," *Ann. N.Y. Acad. Sci.* 1323(1):91-100, Jun. 20, 2014.
Berger-Bachi et al., "Factors influencing methicillin resistance in *Staphylococci,*" *Arch Microbiol.*, 178(3):165-171, Sep. 2002.
Bower et al., "Engineering of bacterial strains and vectors for the production of plasmid DNA," *Appl Microbiol Biotechnol.*, 82(5):805-813, Apr. 2009.
Ertl et al., Technical Issues in Construction of Nucleic Acid Vaccines *Methods.*, 31(3)199-206, 2003.

(Continued)

*Primary Examiner* — Nita M. Minnifield
(74) *Attorney, Agent, or Firm* — Fish & Richardson P.C.

(57) ABSTRACT

This document relates to methods and materials for producing immune responses against polypeptides involved in antibiotic resistance. For example, vaccines against polypeptides involved in antibiotic resistance as well as methods for vaccinating mammals against polypeptides involved in antibiotic resistance are provided.

4 Claims, 2 Drawing Sheets

Specification includes a Sequence Listing.

(56) References Cited

OTHER PUBLICATIONS

International Preliminary Report on Patentability in International Application No. PCT/US2009/048018, dated Jan. 5, 2011, 4 pages.
International Search Report and Written Opinion in International Application No. PCT/US2009/048018, dated Mar. 9, 2010, 7 pages.
Ito et al., "Cloning and Nucleotide Sequence Determination of the Entire mec DNA of Pre-Methicillin-Resistant *Staphylococcus aureus* N315," *Antimicrobial Agents Chemotherapy.*, 43(6):1449-1458, Jun. 1999.
Mariam et al., "Effect of rpoB Mutations Conferring Rifampin Resistance on Fitness of *Mycobacterium tuberculosis*," *Antimicrobial Agents Chemotherapy.*, 48(4):1289-1294, Apr. 2004.
Miller et al., "The rpoB gene of *Mycobacterium tuberculosis*," *Antimicrobial Agents and Chemotherapy.*, 38(4):805-811, Apr. 1994.
Morris et al., "Ancestral antibiotic resistance in *Mycobacterium tuberculosis*," *Proc. Natl. Acad. Sci. USA.*, 102(34):12200-12205, 2005.
Morris et al., "The immunogenicity of single and combination DNA vaccines against tuberculosis," *Vaccine.*, 18:2155-2163, 2000.
Ohwada et al., "DNA vaccination by mecA sequence evokes an antibacterial immune response against methicillin-resistant *Staphylococcus aureus*," *J Antimicrobial Chemotherapy.*, 44:767-774, 1999.
Oliveira et al., "Structural instability of plasmid biopharmaceuticals: challenges and implications," *Trends in Biotechnology.*, 27(9):503-511, Sep. 1, 2009.
rpoB DNA-directed RNA polymerase subunit beta [*Mycobacterium tuberculosis* H37Ry] Gene ID: 888164, created on Aug. 1, 2003, from GenBank.
Williamson et al., "Clinical failures associated with rpoB mutations in phenotypically occult multidrug-resistant *Mycobacterium tuberculosis*," *Int J Tuberc Lung Dis.*, 16(2):216-220, Feb. 2012.

* cited by examiner

Figure 1

Figure 2

METHODS AND MATERIALS FOR PRODUCING IMMUNE RESPONSES AGAINST POLYPEPTIDES INVOLVED IN ANTIBIOTIC RESISTANCE

CROSS-REFERENCE TO RELATED APPLICATIONS

This application is a continuation of U.S. application Ser. No. 14/462,099, filed Aug. 18, 2014 (Abandoned), which is a continuation of U.S. application Ser. No. 13/001,228, filed Feb. 18, 2011 (Abandoned), which is a National Stage application under 35 U.S.C. § 371 that claims the benefit of PCT/US2009/048018, filed Jun. 19, 2009, which claims benefit of priority from U.S. Provisional Application Ser. No. 61/075,881, filed on Jun. 26, 2008. The disclosure of the prior applications are considered part of (and are incorporated by reference in) the disclosure of this application.

BACKGROUND

1. Technical Field

This document relates to methods and materials for producing immune responses against polypeptides involved in antibiotic resistance. For example, this document provides vaccines against polypeptides involved in antibiotic resistance as well as methods for vaccinating mammals against polypeptides involved in antibiotic resistance.

2. Background Information

For many pathogens, reasonably effective antibiotics and vaccines that can temper or control infections, symptoms, and fatalities are available. However, when pathogens become resistant to effective antibiotics, these normally controlled pathogens can become lethal for the patient and can amplify into to epidemics with no effective treatment. Tuberculosis is an example of this problem. *Mycobacterium tuberculosis* (Mtb) can be effectively treated with triple antibiotic therapies. However, use of antibiotics has selected Mtb that is either multi-drug resistant (MDR) or extensively drug resistant (XDR), both of which are substantially more difficult to treat with multi-drug therapy. MDR and XDR Mtb have acquired drug resistance by accumulating multiple gene products that can inactivate or efflux multiple antibiotics.

SUMMARY

This document relates to methods and materials for producing immune responses against polypeptides involved in antibiotic resistance. For example, this document provides vaccines against polypeptides involved in antibiotic resistance as well as methods for vaccinating mammals against polypeptides involved in antibiotic resistance.

In general, one aspect of this document features a method for inducing an immune response against a polypeptide involved in antibiotic resistance. The method comprises, or consists essentially of, administering to an animal (e.g., a mammal) an amount of the polypeptide or a nucleic acid encoding the polypeptide effective for producing the immune response. The polypeptide can be a blaZ polypeptide, a mecA polypeptide, a whiB7 polypeptide, a tap polypeptide, a RV1473 polypeptide, a katG polypeptide, an inhA polypeptide, a rpoB polypeptide, a gidB polypeptide, a pncA polypeptide, an embB polypeptide, or a gyrA polypeptide. The antibiotic resistance can be penicillin-resistance. The antibiotic resistance can be methicillin-resistance. The antibiotic resistance can be vancomycin-resistance. The animal can be a human. The method can comprise administering the polypeptide to the animal. The method can comprise administering the nucleic acid to the animal. The nucleic acid can be a viral vector encoding the polypeptide. The viral vector can be an adenoviral, vaccinia viral, measles, or adeno-associated virus vector. The immune response can reduce the severity of an infection within said animal. The infection can be a *Mycobacterium tuberculosis* infection. The infection can be a *Staphylococcus aureus* infection.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials for producing immune responses against polypeptides involved in antibiotic resistance. For example, this document provides vaccines against polypeptides involved in antibiotic resistance as well as methods for vaccinating mammals against polypeptides involved in antibiotic resistance.

The vaccines provided herein can be in the form of recombinant polypeptides involved in antibiotic resistance or nucleic acid vectors (e.g., viral vectors) designed to express such recombinant polypeptides. The vaccines provided herein can be used to immunize or treat any type of animal including, without limitation, humans, cows, pigs, poultry, dogs, and cats. The vaccines provided herein can be used to induce an immune response against any type of pathogen including, without limitation, intracellular pathogens such as *mycobacterium, chlamydia, rickettsiae, lysteria,* and *brucella* as well as extracellular pathogens such as *staphylococci, streptococci, enterococci, pneumococci,* gram positive bacteria, and *anthrax*. For example, the vaccines provided herein can be designed to target β-lactamase and penicillin binding proteins to treat or prevent community and hospital-acquired bacterial infections such as methicillin-resistant *Staphylococcus aureus*.

Examples of polypeptides involved in antibiotic resistance include, without limitation, a blaZ polypeptide (see Entrez Gene ID: 2859819) from *S. aureus*; a mecA polypeptide (Entrez Gene ID: 2861157) from *S. aureus*; a whiB7 polypeptide from Mtb (Entrez Gene ID: 3205083); a tap polypeptide from Mtb (Entrez Gene ID: 924773); a RV1473 polypeptide from Mtb (Entrez Gene ID: 886549); a katG polypeptide from Mtb (Entrez Gene ID: 885638); an inhA polypeptide from Mtb (Entrez Gene ID: 886523); a rpoB polypeptide from Mtb (Entrez Gene ID: 925979); a gidB polypeptide from Mtb (Entrez Gene ID: 886243); a pncA polypeptide from Mtb (Entrez Gene ID: 888260); an embB polypeptide from Mtb (Entrez Gene ID: 886126); and a gyrA polypeptide from Mtb (Entrez Gene ID: 887105). These polypeptides can include the wild-type sequences of these proteins or variants acquired with mutations that confer drug-resistance. In some cases, a vaccine provided herein can be designed to induce an immune response against a polypeptide involved in antibiotic resistance and one or more polypeptides not involved in antibiotic resistance (e.g., Ag85a of Mtb).

The vaccines provided herein can be used as stand alone vaccines or as adjuvants to other vaccines that target one or more pathogens (e.g., a vaccine that targets multiple Mtb antigens). In some cases, a vaccine provided herein (e.g., a vaccine that targets one or more polypeptides involved in antibiotic resistance) can be delivered in combination with another vaccine (e.g., a BCG vaccine). In some cases, nucleic acid encoding one or more polypeptides involved in antibiotic resistance can be inactivated and introduced into another vaccine (e.g., a BCG vaccine). Genetic engineering can be used to inactivate polypeptides involved in antibiotic resistance by mutating active site amino acids or by expressing the polypeptide as a cocktail of fragments of the full length polypeptide.

Any appropriate method can be used to deliver polypeptides involved in antibiotic resistance to a mammal so that an immune response is induced. For example, nucleic acid encoding a polypeptide involved in antibiotic resistance can be delivered using plasmids or viral vectors such as adenoviral vectors, vaccinia viral vectors, measles, or adeno-associated virus vectors. In some cases, the polypeptides can be produced in bacteria or yeast as purified polypeptide vaccines.

In some cases, a vaccine provided herein can be delivered as a prophylactic vaccine to assist in preventing the production of antibiotic resistance should an infection occur. In some cases, a vaccine provided herein can be applied therapeutically as an adjuvant to antibiotic treatment. For example, upon initiation of multidrug therapy against MDR or XDR, a patient can be vaccinated against Mtb and against one or more polypeptides involved in antibiotic resistance.

The vaccines provided herein can be designed to induce immune responses against one or more (e.g., two, three, four, five, six, seven, or more) polypeptides involved in antibiotic resistance. In some cases, a vaccine can be designed to be patient-specific. For example, a human known to have a particular antibiotic resistant pathogen can be given a vaccine that induces an immune response against the particular polypeptide or polypeptides involved in antibiotic resistance for that pathogen. Any appropriate method can be used to determine the identity of the particular polypeptides involved in antibiotic resistance for a particular pathogen including, without limitation, PCR techniques.

In some cases, polypeptides involved in antibiotic resistance can be used to generate antibodies (e.g., monoclonal antibodies) that can be used alone or in combination with antibiotics to deplete resistance proteins and enhance antibiotic efficacy.

In some cases, a vaccine provided herein (e.g., a vaccine that includes a recombinant polypeptide involve in antibiotic resistance) can be formulated with an adjuvant to form a composition for inducing an immune response when administered to a mammal. An adjuvant can be an immunological compound that can enhance an immune response against a particular antigen such as a polypeptide. Suitable adjuvants include, without limitation, alum as well as other aluminum-based compounds (e.g., $Al_2O_3$) that can be obtained from various commercial suppliers. For example, REHYDRAGEL® adjuvants can be obtained from Reheis Inc. (Berkeley Heights, N.J.). REHYDRAGEL® adjuvants are based on crystalline aluminum oxyhydroxide, and are hydrated gels containing crystalline particles with a large surface area (about 525 $m^2$/g). Their $Al_2O_3$ content typically ranges from about 2 percent to about 10 percent. Rehydragel LG, for example, has an $Al_2O_3$ content of about 6 percent, and flows readily upon slight agitation. Rehydragel LG also has a protein binding capacity of 1.58 (i.e., 1.58 mg of bovine serum albumin bound per 1 mg of $Al_2O_3$), a sodium content of 0.02 percent, a chloride content of 0.28 percent, undetectable sulphate, an arsenic level less than 3 ppm, a heavy metal content less than 15 ppm, a pH of 6.5, and a viscosity of 1090 cp. Rehydragel LG can be combined with a polypeptide solution (e.g., a polypeptide in PBS) to yield $Al(OH)_3$. In addition, ALHYDROGEL™, an aluminum hydroxy gel adjuvant, (Alhydrogel 1.3%, Alhydrogel 2.0%, or Alhydrogel "85") obtained from Brenntag Stinnes Logistics can be used.

In some cases, MN51 can be combined with a vaccine provided herein to form a composition that elicits an immune response when administered to a mammal. MN51 (MONTANIDE® Incomplete SEPPIC Adjuvant (ISA) 51) as well as MN720 are available from Seppic (Paris, France). MN51 contains mannide oleate (MONTANIDE® 80, also known as anhydro mannitol octadecenoate) in mineral oil solution (Drakeol 6 VR). MONTANIDE® 80 is a limpid liquid with a maximum acid value of 1, a saponification value of 164-172, a hydroxyl value of 89-100, an iodine value of 67-75, a maximum peroxide value of 2, a heavy metal value less than 20 ppm, a maximum water content of 0.35%, a maximum color value of 9, and a viscosity at 25° C. of about 300 mPas. MONTANIDE® associated with oil (e.g., mineral oil, vegetable oil, squalane, squalene, or esters) is known as MONTANIDE® ISA. Drakeol 6 VR is a pharmaceutical grade mineral oil. Drakeol 6 VR contains no unsaturated or aromatic hydrocarbons, and has an A.P.I. gravity of 36.2-36.8, a specific gravity at 25° C. of 0.834-0.838, a viscosity at 100° F. of 59-61 SSU or 10.0-10.6 centistokes, a refractive index at 25° C. of 1.458-1.463, a better than minimum acid test, is negative for fluorescence at 360 nm, is negative for visible suspended matter, has an ASTM pour test value of 0-15° F., has a minimum ASTM flash point of 295° F., and complies with all RN requirements for light mineral oil and ultraviolet absorption. MN51 contains about 8 to 12 percent anhydro mannitol octadecenoate and about 88 to 92 percent mineral oil.

Other adjuvants include immuno-stimulating complexes (ISCOMs) that can contain such components as cholesterol and saponins. ISCOM matrices can be prepared and conjugated to $Cu^{2+}$ using methods such as those described herein. Adjuvants such as FCA, FIA, MN51, MN720, and $Al(OH)_3$ are commercially available from companies such as Seppic, Difco Laboratories (Detroit, Mich.), and Superfos Biosector A/S (Vedbeak, Demark).

Other immunostimulatory components include, without limitation, muramyldipeptide (e.g., N-acetylmuramyl-L-alanyl-D-isoglutamine; MDP), monophosphoryl-lipid A (MPL), formyl-methionine containing tripeptides such as N-formyl-Met-Leu-Phe, or a bacterial lipopolysaccharide. Such compounds are commercially available from Sigma Chemical Co. (St. Louis, Mo.) and RIBI ImmunoChem Research, Inc. (Hamilton, Mont.), for example. Additional immunostimulatory components can include pneumovax (an approved human vaccine), CD40L, or IL-12. In some embodiments, an adjuvant can be Complete Freund's Adjuvant or Incomplete Freund's Adjuvant.

This document also provides methods for preparing a vaccine provided herein. Such methods can involve suspending an amount of a nucleic acid vector (e.g., viral vector) or a polypeptide in a suitable amount of a physiological buffer (e.g., PBS). The nucleic acid vector or polypeptide then can be combined with a suitable amount of an adjuvant/immunostimulatory compound. The combining step can be achieved by any appropriate method, including, for example, stirring, shaking, vortexing, or passing back and forth through a needle attached to a syringe.

It is noted that the compositions can be prepared in batch, such that enough unit doses are obtained for multiple injections (e.g., injections into multiple mammals or multiple injections into the same mammal). A "unit dose" of a composition provided herein refers to the amount of a composition administered to a mammal at one time. A unit dose of the compositions provided herein can contain any amount of polypeptides involved in antibiotic resistance or nucleic acid encoding such polypeptides. For example, a unit dose of a composition can contain between about 0.1 µg and about 1 g (e.g., 1 µg, 10 µg, 15 µg, 25 µg, 30 µg, 50 µg, 100 µg, 250 µg, 280 µg, 300 µg, 500 µg, 750 µg, 1 mg, 10 mg, 15 mg, 25 mg, 30 mg, 50 mg, 100 mg, 250 mg, 280 mg, 300 mg, 500 mg, 750 mg, or more) of one or more polypeptides involved in antibiotic resistance. In the case of viral vectors, a unit dose of a composition can have a titer between about $10^3$ to $10^{10}$ (e.g., $10^3$, $10^4$, $10^5$, $10^6$, $10^7$, $10^8$, $10^9$, or $10^{10}$) viral particles or plaque forming units.

Methods for inducing a particular immune response in a mammal (e.g., a mouse, a rat, a cat, a dog, a horse, a cow, a non-human primate such as a cynomolgus monkey, or a human) include, without limitation, administering to a mammal an amount of a vaccine provided herein that is effective for producing an antibody response against one or more polypeptides involved in antibiotic resistance.

The vaccines provided herein can be administered using any appropriate method. Administration can be, for example, topical (e.g., transdermal, ophthalmic, or intranasal); pulmonary (e.g., by inhalation or insufflation of powders or aerosols); oral; or parenteral (e.g., by subcutaneous, intrathecal, intraventricular, intramuscular, or intraperitoneal injection, or by intravenous drip). Administration can be rapid (e.g., by injection) or can occur over a period of time (e.g., by slow infusion or administration of slow release formulations).

The invention will be further described in the following examples, which do not limit the scope of the invention described in the claims.

EXAMPLES

Example 1—Plasmids Containing Codon-Optimized Antigens

Codon-optimized sequences for Mtb antigens are obtained from Genscript Corporation (Piscataway, N.J.) or generated using molecular cloning techniques. These sequences are codon-optimized for expression in mammalian cells for use as gene-based vaccines. The following Mtb genes that are expressed by H37Rv, MDR Mtb, or XDR Mtb or those listed in Table 1 that are expressed by H37Rv, MDR Mtb, or XDR Mtb are synthesized and cloned into the pShuttle-CMV plasmid:

Ag85a: Positive control protective antigen.

whiB7: Inducer of expression of a regulon of Mtb genes involved in antibiotic resistance (including tap, RV1473, and erm (Morris et al., *Proc. Nat'l. Acad. Sci. USA*, 102(34): 12200-12205 (2005)).

tap: Drug efflux pump conferring low level resistance to aminoglyosides and tetracycline.

RV1473: Putative macrolide transporter induced by whiB7 (Morris et al., *Proc. Nat'l. Acad. Sci. USA*, 102(34): 12200-12205 (2005)).

erm: Confers resistance to macrolide, lincosamide, and streptogramin.

TABLE 1

Genes involved in antibiotic resistance in *Mycobacterium tuberculosis*.

| Drug Resistance | MDR | XDR |
|---|---|---|
| Inh | katG (S315T) | katG (S315T) |
| Inh | inhA -8TA | inhA -8TA |
| Rif | rpoB (N487S) | rpoB (D435Y, L452P) |
| Streptomycin | gidB Δ | gidB Δ |
| Pyrazinamide | pncA (A132G) | pncA Δ |
| Ethambutol | embB (M306V) | embB (M306V) |
| Ofloxacin | | gyrA A90V |
| Kanamycin | | rrsA1401G |

Where more than one mutant is shown in ( ), the other mutations are introduced by site-directed mutagenesis. Point mutations are likely irrelevant to generating cellular immunity since it is unlikely that these mutations will fall within MHC I or II epitopes.

Codon-optimized sequences for antigens from *Staphylococcus aureus* or other gram-positive bacteria, included those listed in Table 2, are generated using molecular cloning techniques. These sequences are codon-optimized for expression in mammalian cells for use as gene-based vaccines.

TABLE 2

Genes involved in antibiotic resistance in *Staphylococcus aureus* and other gram-positive bacteria

| Drug Resistance | MSSA | MRSA | VRSA |
|---|---|---|---|
| Penicillin | BlaZ | | BlaZ |
| Methicillin | — | MecA | MecA |
| Vancomycin | — | | VanS |
| Vancomycin | — | | VanT |

MSSA is sensitive, penicillin-resistant *S. aureus*
MRSA is methicillin-resistant *S. aureus*
VRSA is vancomycin-resistant *S. aureus*

Example 2—Adenovirus Vectors Containing Codon-Optimized Antigens

Ad5 vectors are used to generate gene-based vaccines, which are used as an effective vaccine delivery vehicle in mice. Any appropriate vaccine carrier including *Bacillus*

Calmette-Guerin (BCG) or vaccinia is used as a vaccine delivery vehicle in humans. In some cases, the recombinant polypeptides are delivered directly to the mammal (e.g., a human).

Once the pShuttle-CMV vectors are obtained, they are recombined into the Ad5 genome in bacteria and are used to generate CsCl-purified Ad5 vaccines.

Example 3—Codon-Optimized Gene for *S. aureus* BlaZ

The following codon-optimized nucleic acid sequence was generated to encode an *S. aureus* BlaZ polypeptide:

```
(SEQ ID NO: 1)
AAGGAGCTGAACGACCTGGAGAAGAAGTACAACGCCC-
ACATCGGCGTGTACGCCCTGGACACCAAGAGCGGCAAGGAGGTGAAGTT
CAACAGCGACAAGCGCTTCGCCTACGCCAGCACCAGCAAGGCCATCAAC
AGCGCCATCCTGCTGGAGCAGGTGCCCTACAACAAGCTGAACAAGAAGG
TGCACATCAACAAGGACGACATCGTGGCCTACAGCCCCATCCTGGAGAA
GTACGTGGGCAAGGACATCACCCTGAAGGCCCTGATCGAGGCCAGCATG
ACCTACAGCGACAACACCGCCAACAACAAGATCATCAAGGAGATCGGCG
GCATCAAGAAGGTGAAGCAGCGCCTGAAGGAGCTGGGCGACAAGGTGA
CCAACCCCGTGCGCTACGAGATCGAGCTGAACTACTACAGCCCCAAGAG
CAAGAAGGACACCAGCACCCCCGCCGCCTTCGGCAAGACCCTGAACAAG
CTGATCGCCAACGGCAAGCTGAGCAAGGAGAACAAGAAGTTCCTGCTGG
ACCTGATGCTGAACAACAAGAGCGGCGACACCCTGATCAAGGACGGCGT
GCCCAAGGACTACAAGGTGGCCGACAAGAGCGGCCAGGCCATCACCTAC
GCCAGCCGCAACGACGTGGCCTTCGTGTACCCCAAGGGCCAGAGCGAGC
CCATCGTGCTGGTGATCTTCACCAACAAGGACAACAAGAGCGACAAGCC
CAACGACAAGCTGATCAGCGAGACCGCCAAGAGCGTGATGAAGGAGTTC.
```

The amino acid sequence encoded by SEQ ID NO:1 is as follows:

```
(SEQ ID NO: 2)
KELNDLEKKYNAHIGVYALDTKSGKEVKFNSDKRFAYASTSKAINSAIL
LEQ-VPYNKLNKKVHINKDDIVAYSPILEKYVGKDITLKALIEASMTYSD
NTANNKIIKEIGGIKKVKQRLKELGDKVTNPVRYEIELNYYSPKSKKDTS
TPAAFGKTLNKLIANGKLSKENKKFLLDLMLNNKSGDTLIKDGVPKDYKV
ADKSGQAITYASRNDVAFVYPKGQSEPIVLVIFTNKDNKSDKPNDKLISE
TAKSVMKEF.
```

Figure 1:
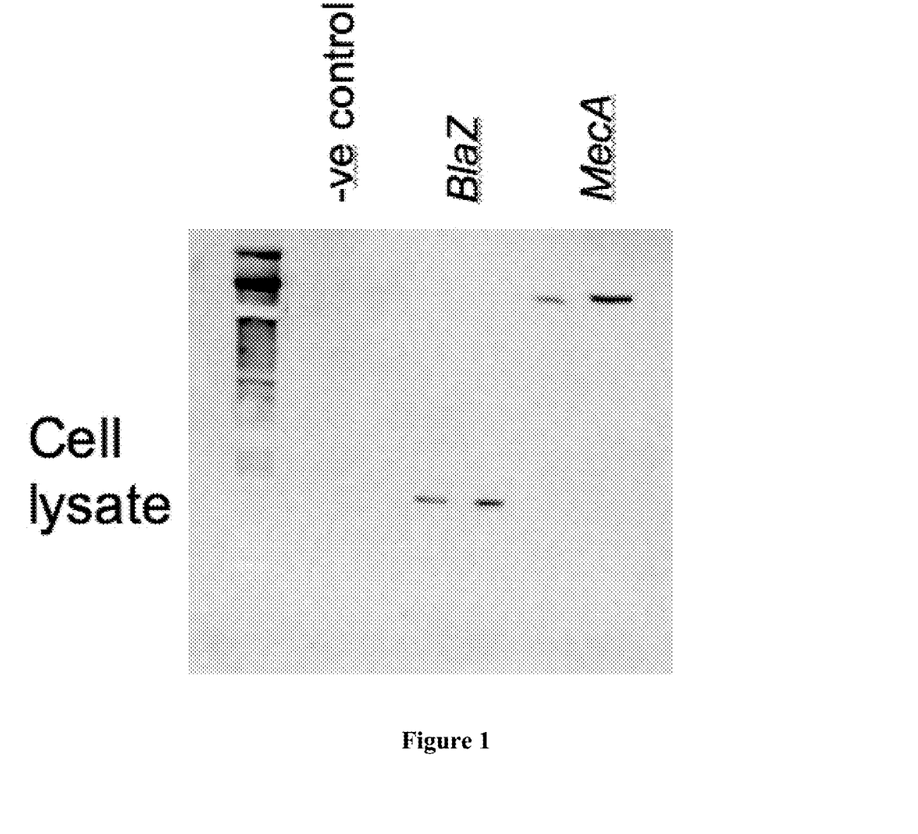
FIG. 1 is a photograph of a western blot of cell lysates obtained from mammalian cells that were transfected with plasmids expressing either a BlaZ polypeptide or a MecA polypeptide. Proteins were detected with a anti-His6 antibody recognizing a His6 tag on the c-terminus of each of the proteins. The left band are normal cells. The right band of each set are cells expressing Rad23 that inhibits proteasome degradation of proteins. The negative control (-ve control) is a lysate of cells transfected with GFP gene.

The codon-optimized nucleic acid encoding a BlaZ polypeptide was cloned into a shuttle plasmid fusing the sequence to the alpha 1-anti-trypsin secretory leader. Expression in cell lines generated detectable amounts of polypeptide from mammalian cells (FIG. 1).

Figure 2:
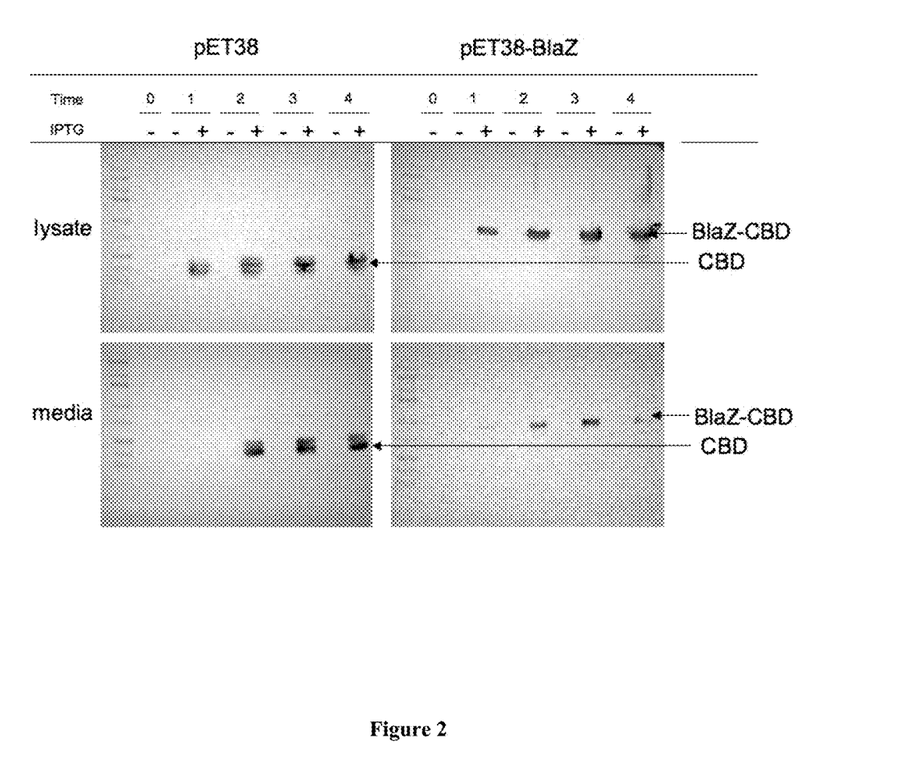
FIG. 2 is photograph of Western blot of BlaZ polypeptides purified from a cell lysate and from the media of bacterial cells. CBD designates the cellulose binding domain fusion tag of the pET38 vector. BlaZ-CBD is the fusion of BlaZ to the CBD tag.

Polypeptide vaccines can be produced from bacterial expression plasmids. The sequence of SEQ ID NO:1 was cloned into a pET-38 plasmid fusing it to a cellulose binding domain (CBD) and a His6 tag for purification. Expression of the polypeptide from bacteria followed by Western blotting revealed the presence of the polypeptide intracellularly in cell lysates and in a form secreted into the media (FIG. 2).

Example 4—Codon-Optimized Gene for *S. aureus* MecA

The following codon-optimized nucleic acid sequence was generated to encode an *S. aureus* MecA polypeptide:

```
(SEQ ID NO: 3)
AGCAAGGACAAGGAGATCAACAACACCATCGACGC-
CATCGAGGACAAGAACTTCAAGCAGGTGTACAAGGACAGCAGCTACATC
AGCAAGAGCGACAACGGCGAGGTGGAGATGACCGAGCGCCCCATCAAGA
TCTACAACAGCCTGGGCGTGAAGGACATCAACATCCAGGACCGCAAGAT
CAAGAAGGTGAGCAAGAACAAGAAGCGCGTGGACGCCCAGTACAAGATC
AAGACCAACTACGGCAACATCGACCGCAACGTGCAGTTCAACTTCGTGA
AGGAGGACGGCATGTGGAAGCTGGACTGGGACCACAGCGTGATCATCCC
CGGCATGCAGAAGGACCAGAGCATCCACATCGAGAACCTGAAGAGCGAG
CGCGGCAAGATCCTGGACCGCAACAACGTGGAGCTGGCCAACACCGGCA
CCGCCTACGAGATCGGCATCGTGCCCAAGAACGTGAGCAAGAAGGACTA
CAAGGCCATCGCCAAGGAGCTGAGCATCAGCGAGGACTACATCAAGCAG
CAGATGGACCAGAACTGGGTGCAGGACGACACCTTCGTGCCCCTGAAGA
CCGTGAAGAAGATGGACGAGTACCTGAGCGACTTCGCCAAGAAGTTCCA
CCTGACCACCAACGAGACCGAGAGCCGCAACTACCCCCTGGGCAAGGCC
ACCAGCCACCTGCTGGGCTACGTGGGCCCCATCAACAGCGAGGAGCTGA
AGCAGAAGGAGTACAAGGGCTACAAGGACGACGCCGTGATCGGCAAGAA
GGGCCTGGAGAAGCTGTACGACAAGAAGCTGCAGCACGAGGACGGCTAC
CGCGTGACCATCGTGGACGACAACAGCAACACCATCGCCCACACCCTGA
TCGAGAAGAAGAAGGACGGCAAGGACATCCAGCTGACCATCGACGC
CAAGGTGCAGAAGAGCATCTACAACAACATGAAGAACGACTACGGCAGC
GGCACCGCCATCCACCCCCAGACCGGCGAGCTGCTGGCCCTGGTGAGCA
CCCCCAGCTACGACGTGTACCCCTTCATGTACGGCATGAGCAACGAGGA
GTACAACAAGCTGACCGAGGACAAGAAGGAGCCCCTGCTGAACAAGTTC
CAGATCACCACCAGCCCCGGCAGCACCCAGAAGATCCTGACCGCCATGA
TCGGCCTGAACAACAAGACCCTGGACGACAAGACCAGCTACAAGATCGA
CGGCAAGGGCTGGCAGAAGGACAAGAGCTGGGGCGGCTACAACGTGACC
CGCTACGAGGTGGTGAACGGCAACATCGACCTGAAGCAGGCCATCGAGA
GCAGCGACAACATCTTCTTCGCCCGCGTGGCCCTGGAGCTGGGCAGCAA
GAAGTTCGAGAAGGGCATGAAGAAGCTGGGCGTGGGCGAGGACATCCCC
AGCGACTACCCCTTCTACAACGCCCAGATCAGCAACAAGAACCTGGACA
ACGAGATCCTGCTGGCCGACAGCGGCTACGGCCAGGGCGAGATCCTGAT
CAACCCCGTGCAGATCCTGAGCATCTACAGCGCCCTGGAGAACAACGGC
AACATCAACGCCCCCACCTGCTGAAGGACACCAAGAACAAGGTGTGGA
AGAAGAACATCATCAGCAAGGAGAACATCAACCTGCTGACCGACGGCAT
GCAGCAGGTGGTGAACAAGACCCACAAGGAGGACATCTACCGCAGCTAC
```

-continued

GCCAACCTGATCGGCAAGAGCGGCACCGCCGAGCTGAAGATGAAGCAGG

GCGAGACCGGCCGCCAGATCGGCTGGTTCATCAGCTACGACAAGGACAA

CCCCAACATGATGATGGCCATCAACGTGAAGGACGTGCAGGACAAGGGC

ATGGCCAGCTACAACGCCAAGATCAGCGGCAAGGTGTACGACGAGCTGT

ACGAGAACGGCAACAAGAAGTACGACATCGACGAG.

The amino acid sequence encoded by SEQ ID NO:3 is as follows:

(SEQ ID NO: 4)
SKDK-

EINNTIDAIEDKNFKQVYKDSSYISKSDNGEVEMTERPIKIYNSLGVKDI

NIQDRKIKKVSKNKKRVDAQYKIKTNYGNIDRNVQFNFVKEDGMWKLDWD

HSVIIPGMQKDQSIHIENLKSERGKILDRNNVELANTGTAYEIGIVPKNV

SKKDYKAIAKELSISEDYIKQQMDQNWVQDDTFVPLKTVKKMDEYLSDFA

KKFHLTTNETESRNYPLGKATSHLLGYVGPINSEELKQKEYKGYKDDAVI

GKKGLEKLYDKKLQHEDGYRVTIVDDNSNTIAHTLIEKKKKDGKDIQLTI

DAKVQKSIYNNMKNDYGSGTAIHPQTGELLALVSTPSYDVYPFMYGMSNE

EYNKLTEDKKEPLLNKFQITTSPGSTQKILTAMIGLNNKTLDDKTSYKID

GKGWQKDKSWGGYNVTRYEVVNGNIDLKQAIESSDNIFFARVALELGSKK

FEKGMKKLGVGEDIPSDYPFYNAQISNKNLDNEILLADSGYGQGEILINP

VQILSIYSALENNGNINAPHLLKDTKNKVWKKNIISKENINLLTDGMQQV

VNKTHKEDIYRSYANLIGKSGTAELKMKQGETGRQIGWFISYDKDNPNMM

MAINVKDVQDKGMASYNAKISGKVYDELYENGNKKYDIDE.

The codon-optimized nucleic acid encoding a MecA polypeptide was cloned into a shuttle plasmid fusing the sequence to the alpha 1-anti-trypsin secretory leader.

Expression in cell lines generated detectable amounts of polypeptide from mammalian cells (FIG. 1).

Example 5—Administration of Vaccine

Separate groups of 50 BALB/c mice are immunized intranasally with $10^{10}$ virus particles of Ad vaccines expressing the following antigens: saline; GFP (negative control vaccine for Mtb); Ag85a (positive control for CD8 responses and protection); and whiB7, tap, RV1473 and erm (vaccines against polypeptides involved in antibiotic resistance). Additional groups are used for the genes listed in Table 1. Four weeks later, five mice from each group are evaluated for cellular immune responses using, e.g., ELISPOT, intracellular cytokine staining. At the same time, the remaining mice of each group are challenged with 300 colony forming units of H37Rv/mouse by aerosolization to mimic the normal Mtb infection route. H37Rv is not classified as MDR or XDR, but is resistant to a number of antibiotics (Morris et al., *Proc. Nat'l. Acad. Sci. USA,* 102(34):12200-12205 (2005)). In a separate study, legitimate MDR or XDR Mtb is used in place of H37Rv. At 2, 4, 16, and 32 weeks post-infection (WPI), ten mice from each group are sacrificed, and Mtb is titered from the lung and the spleen. Histopathology and MST testing are also performed on the samples. The remaining mice are retained to estimate median survival time (MST). Control animals typically survive until 30 weeks with longer survival for successful vaccines. At 48 weeks, all animals are sacrificed for titering and histopathology.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for inducing an immune response against an intracellular *Mycobacterium tuberculosis* pathogen that is resistant to an antibiotic in a human having an infection with said intracellular *Mycobacterium tuberculosis* pathogen, wherein said method comprises administering to said human an amount of a nucleic acid encoding a whiB7 polypeptide effective for producing said immune response in said human that reduces the severity of said infection within said human, wherein said whiB7 polypeptide is involved in antibiotic resistance.

2. The method of claim 1, wherein said method comprises administering said nucleic acid to said human.

3. The method of claim 2, wherein said nucleic acid is a viral vector encoding said polypeptide.

4. The method of claim 3, wherein said viral vector is an adenoviral, vaccinia viral, measles, or adeno-associated virus vector.

* * * * *

SEQUENCE LISTING

<160> NUMBER OF SEQ ID NOS: 4

<210> SEQ ID NO 1
<211> LENGTH: 771
<212> TYPE: DNA
<213> ORGANISM: Staphylococcus aureus

<400> SEQUENCE: 1

```
aaggagctga acgacctgga gaagaagtac aacgcccaca tcggcgtgta cgccctggac      60
accaagagcg gcaaggaggt gaagttcaac agcgacaagc gcttcgccta cgccagcacc     120
agcaaggcca tcaacagcgc catcctgctg gagcaggtgc cctacaacaa gctgaacaag     180
aaggtgcaca tcaacaagga cgacatcgtg gcctacagcc ccatcctgga gaagtacgtg     240
ggcaaggaca tcaccctgaa ggccctgatc gaggccagca tgacctacag cgacaacacc     300
gccaacaaca agatcatcaa ggagatcggc ggcatcaaga aggtgaagca gcgcctgaag     360
gagctgggcg acaaggtgac caacccgtg cgctacgaga tcgagctgaa ctactacagc     420
cccaagagca agaaggacac cagcaccccc gccgccttcg gcaagaccct gaacaagctg     480
atcgccaacg gcaagctgag caaggagaac aagaagttcc tgctggacct gatgctgaac     540
```

```
aacaagagcg gcgacaccct gatcaaggac ggcgtgccca aggactacaa ggtggccgac      600
aagagcggcc aggccatcac ctacgccagc cgcaacgacg tggccttcgt gtaccccaag      660
ggccagagcg agcccatcgt gctggtgatc ttcaccaaca aggacaacaa gagcgacaag      720
cccaacgaca agctgatcag cgagaccgcc aagagcgtga tgaaggagtt c              771
```

<210> SEQ ID NO 2
<211> LENGTH: 257
<212> TYPE: PRT
<213> ORGANISM: Staphylococcus aureus

<400> SEQUENCE: 2

```
Lys Glu Leu Asn Asp Leu Glu Lys Lys Tyr Asn Ala His Ile Gly Val
1               5                  10                  15

Tyr Ala Leu Asp Thr Lys Ser Gly Lys Glu Val Lys Phe Asn Ser Asp
            20                  25                  30

Lys Arg Phe Ala Tyr Ala Ser Thr Ser Lys Ala Ile Asn Ser Ala Ile
        35                  40                  45

Leu Leu Glu Gln Val Pro Tyr Asn Lys Leu Asn Lys Lys Val His Ile
    50                  55                  60

Asn Lys Asp Asp Ile Val Ala Tyr Ser Pro Ile Leu Glu Lys Tyr Val
65                  70                  75                  80

Gly Lys Asp Ile Thr Leu Lys Ala Leu Ile Glu Ala Ser Met Thr Tyr
                85                  90                  95

Ser Asp Asn Thr Ala Asn Asn Lys Ile Ile Lys Glu Ile Gly Gly Ile
            100                 105                 110

Lys Lys Val Lys Gln Arg Leu Lys Glu Leu Gly Asp Lys Val Thr Asn
        115                 120                 125

Pro Val Arg Tyr Glu Ile Glu Leu Asn Tyr Tyr Ser Pro Lys Ser Lys
    130                 135                 140

Lys Asp Thr Ser Thr Pro Ala Ala Phe Gly Lys Thr Leu Asn Lys Leu
145                 150                 155                 160

Ile Ala Asn Gly Lys Leu Ser Lys Glu Asn Lys Lys Phe Leu Leu Asp
                165                 170                 175

Leu Met Leu Asn Asn Lys Ser Gly Asp Thr Leu Ile Lys Asp Gly Val
            180                 185                 190

Pro Lys Asp Tyr Lys Val Ala Asp Lys Ser Gly Gln Ala Ile Thr Tyr
        195                 200                 205

Ala Ser Arg Asn Asp Val Ala Phe Val Tyr Pro Lys Gly Gln Ser Glu
    210                 215                 220

Pro Ile Val Leu Val Ile Phe Thr Asn Lys Asp Asn Lys Ser Asp Lys
225                 230                 235                 240

Pro Asn Asp Lys Leu Ile Ser Glu Thr Ala Lys Ser Val Met Lys Glu
                245                 250                 255

Phe
```

<210> SEQ ID NO 3
<211> LENGTH: 1932
<212> TYPE: DNA
<213> ORGANISM: Staphylococcus aureus

<400> SEQUENCE: 3

```
agcaaggaca aggagatcaa caacaccatc gacgccatcg aggacaagaa cttcaagcag       60
gtgtacaagg acagcagcta catcagcaag agcgacaacg gcgaggtgga gatgaccgag      120
cgccccatca agatctacaa cagcctgggc gtgaaggaca tcaacatcca ggaccgcaag      180
```

```
atcaagaagg tgagcaagaa caagaagcgc gtggacgccc agtacaagat caagaccaac    240
tacggcaaca tcgaccgcaa cgtgcagttc aacttcgtga aggaggacgg catgtggaag    300
ctggactggg accacagcgt gatcatcccc ggcatgcaga aggaccagag catccacatc    360
gagaacctga gagcgagcg cggcaagatc ctggaccgca caacgtgga gctggccaac    420 accggcaccg cctacgagat cggcatcgtg cccaagaacg tgagcaagaa ggactacaag    480
gccatcgcca aggagctgag catcagcgag gactacatca gcagcagat ggaccagaac    540 tgggtgcagg acgacacctt cgtgcccctg aagaccgtga agaagatgga cgagtacctg    600
agcgacttcg ccaagaagtt ccacctgacc accaacgaga ccgagagccg caactacccc    660
ctgggcaagg ccaccagcca cctgctgggc tacgtgggcc ccatcaacag cgaggagctg    720
aagcagaagg agtacaaggg ctacaaggac gacgccgtga tcggcaagaa gggcctggag    780
aagctgtacg acaagaagct gcagcacgag gacggctacc gcgtgaccat cgtggacgac    840
aacagcaaca ccatcgccca cccctgatc gagaagaaga gaaggacgg caaggacatc    900 cagctgacca tcgacgccaa ggtgcagaag agcatctaca caacatgaa gaacgactac    960 ggcagcggca ccgccatcca ccccagacc ggcgagctgc tggccctggt gagcaccccc   1020
agctacgacg tgtaccccctt catgtacggc atgagcaacg aggagtacaa caagctgacc   1080
gaggacaaga aggagcccct gctgaacaag ttccagatca ccaccagccc cggcagcacc   1140
cagaagatcc tgaccgccat gatcggcctg aacaacaaga ccctggacga caagaccagc   1200
tacaagatcg acggcaaggg ctggcagaag gacaagagct ggggcggcta caacgtgacc   1260
cgctacgagg tggtgaacgg caacatcgac ctgaagcagg ccatcgagag cagcgacaac   1320
atcttcttcg cccgcgtggc cctggagctg ggcagcaaga gttcgagaa gggcatgaag   1380 aagctgggcg tgggcgagga catccccagc gactacccct tctacaacgc ccagatcagc   1440
aacaagaacc tggacaacga gatcctgctg gccgacagcg gctacggcca gggcgagatc   1500
ctgatcaacc ccgtgcagat cctgagcatc tacagcgccc tggagaacaa cggcaacatc   1560 aacgccccc acctgctgaa ggacaccaag aacaaggtgt ggaagaagaa catcatcagc   1620
aaggagaaca tcaacctgct gaccgacggc atgcagcagg tggtgaacaa gacccacaag   1680
gaggacatct accgcagcta cgccaacctg atcggcaaga gcggcaccgc cgagctgaag   1740
atgaagcagg cgagaccgg ccgccagatc ggctggttca tcagctacga caaggacaac   1800
cccaacatga tgatggccat caacgtgaag gacgtgcagg acaagggcat ggccagctac   1860
aacgccaaga tcagcggcaa ggtgtacgac gagctgtacg agaacggcaa caagaagtac   1920
gacatcgacg ag                                                        1932
```

<210> SEQ ID NO 4
<211> LENGTH: 644
<212> TYPE: PRT
<213> ORGANISM: Staphylococcus aureus

<400> SEQUENCE: 4

```
Ser Lys Asp Lys Glu Ile Asn Asn Thr Ile Asp Ala Ile Glu Asp Lys
  1               5                  10                  15

Asn Phe Lys Gln Val Tyr Lys Asp Ser Ser Tyr Ile Ser Lys Ser Asp
             20                  25                  30

Asn Gly Glu Val Glu Met Thr Glu Arg Pro Ile Lys Ile Tyr Asn Ser
         35                  40                  45

Leu Gly Val Lys Asp Ile Asn Ile Gln Asp Arg Lys Ile Lys Lys Val
```

```
                50                  55                  60
Ser Lys Asn Lys Lys Arg Val Asp Ala Gln Tyr Lys Ile Lys Thr Asn
 65                  70                  75                  80

Tyr Gly Asn Ile Asp Arg Asn Val Gln Phe Asn Phe Val Lys Glu Asp
                     85                  90                  95

Gly Met Trp Lys Leu Asp Trp Asp His Ser Val Ile Ile Pro Gly Met
                100                 105                 110

Gln Lys Asp Gln Ser Ile His Ile Glu Asn Leu Lys Ser Glu Arg Gly
                115                 120                 125

Lys Ile Leu Asp Arg Asn Asn Val Glu Leu Ala Asn Thr Gly Thr Ala
                130                 135                 140

Tyr Glu Ile Gly Ile Val Pro Lys Asn Val Ser Lys Lys Asp Tyr Lys
145                 150                 155                 160

Ala Ile Ala Lys Glu Leu Ser Ile Ser Glu Asp Tyr Ile Lys Gln Gln
                165                 170                 175

Met Asp Gln Asn Trp Val Gln Asp Asp Thr Phe Val Pro Leu Lys Thr
                180                 185                 190

Val Lys Lys Met Asp Glu Tyr Leu Ser Asp Phe Ala Lys Lys Phe His
                195                 200                 205

Leu Thr Thr Asn Glu Thr Glu Ser Arg Asn Tyr Pro Leu Gly Lys Ala
210                 215                 220

Thr Ser His Leu Leu Gly Tyr Val Gly Pro Ile Asn Ser Glu Glu Leu
225                 230                 235                 240

Lys Gln Lys Glu Tyr Lys Gly Tyr Lys Asp Asp Ala Val Ile Gly Lys
                245                 250                 255

Lys Gly Leu Glu Lys Leu Tyr Asp Lys Lys Leu Gln His Glu Asp Gly
                260                 265                 270

Tyr Arg Val Thr Ile Val Asp Asp Asn Ser Asn Thr Ile Ala His Thr
                275                 280                 285

Leu Ile Glu Lys Lys Lys Lys Asp Gly Lys Asp Ile Gln Leu Thr Ile
                290                 295                 300

Asp Ala Lys Val Gln Lys Ser Ile Tyr Asn Asn Met Lys Asn Asp Tyr
305                 310                 315                 320

Gly Ser Gly Thr Ala Ile His Pro Gln Thr Gly Glu Leu Leu Ala Leu
                325                 330                 335

Val Ser Thr Pro Ser Tyr Asp Val Tyr Pro Phe Met Tyr Gly Met Ser
                340                 345                 350

Asn Glu Glu Tyr Asn Lys Leu Thr Glu Asp Lys Lys Glu Pro Leu Leu
                355                 360                 365

Asn Lys Phe Gln Ile Thr Thr Ser Pro Gly Ser Thr Gln Lys Ile Leu
                370                 375                 380

Thr Ala Met Ile Gly Leu Asn Asn Lys Thr Leu Asp Asp Lys Thr Ser
385                 390                 395                 400

Tyr Lys Ile Asp Gly Lys Gly Trp Gln Lys Asp Lys Ser Trp Gly Gly
                405                 410                 415

Tyr Asn Val Thr Arg Tyr Glu Val Val Asn Gly Asn Ile Asp Leu Lys
                420                 425                 430

Gln Ala Ile Glu Ser Ser Asp Asn Ile Phe Phe Ala Arg Val Ala Leu
                435                 440                 445

Glu Leu Gly Ser Lys Lys Phe Glu Lys Gly Met Lys Lys Leu Gly Val
                450                 455                 460

Gly Glu Asp Ile Pro Ser Asp Tyr Pro Phe Tyr Asn Ala Gln Ile Ser
465                 470                 475                 480
```

-continued

```
Asn Lys Asn Leu Asp Asn Glu Ile Leu Leu Ala Asp Ser Gly Tyr Gly
            485             490             495

Gln Gly Glu Ile Leu Ile Asn Pro Val Gln Ile Leu Ser Ile Tyr Ser
            500             505             510

Ala Leu Glu Asn Asn Gly Asn Ile Asn Ala Pro His Leu Leu Lys Asp
            515             520             525

Thr Lys Asn Lys Val Trp Lys Lys Asn Ile Ile Ser Lys Glu Asn Ile
    530             535             540

Asn Leu Leu Thr Asp Gly Met Gln Gln Val Val Asn Lys Thr His Lys
545             550             555             560

Glu Asp Ile Tyr Arg Ser Tyr Ala Asn Leu Ile Gly Lys Ser Gly Thr
                565             570             575

Ala Glu Leu Lys Met Lys Gln Gly Glu Thr Gly Arg Gln Ile Gly Trp
            580             585             590

Phe Ile Ser Tyr Asp Lys Asp Asn Pro Asn Met Met Met Ala Ile Asn
        595             600             605

Val Lys Asp Val Gln Asp Lys Gly Met Ala Ser Tyr Asn Ala Lys Ile
    610             615             620

Ser Gly Lys Val Tyr Asp Glu Leu Tyr Glu Asn Gly Asn Lys Lys Tyr
625             630             635             640

Asp Ile Asp Glu
```